(12) United States Patent
Yang et al.

(10) Patent No.: US 7,276,486 B2
(45) Date of Patent: Oct. 2, 2007

(54) COMPOSITIONS FOR VAGINAL TREATMENT

(75) Inventors: Shu-Ping Yang, Alpharetta, GA (US); Yanbin Huang, Roswell, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 472 days.

(21) Appl. No.: 10/801,063

(22) Filed: Mar. 15, 2004

(65) Prior Publication Data

US 2005/0203032 A1 Sep. 15, 2005

(51) Int. Cl.
*A61K 31/7004* (2006.01)
(52) U.S. Cl. .................................................. 514/23
(58) Field of Classification Search .................. 514/23
See application file for complete search history.

(56) References Cited

U.S. PATENT DOCUMENTS

| | | | |
|---|---|---|---|
| 5,520,926 A * | 5/1996 | Ferguson | 424/443 |
| 6,159,491 A | 12/2000 | Durrani | |
| 6,294,521 B1 * | 9/2001 | Cowden | 514/23 |
| 6,416,779 B1 | 7/2002 | D'Augustine et al. | |
| 6,486,207 B2 | 11/2002 | Yeager et al. | |
| 6,632,796 B1 | 10/2003 | Zeng | |

FOREIGN PATENT DOCUMENTS

| | | |
|---|---|---|
| EP | 1199069 A2 | 4/2002 |
| EP | 1249247 A2 | 10/2002 |
| WO | WO-9001938 A1 | 3/1990 |
| WO | WO-2005/094840 A1 | 10/2005 |

OTHER PUBLICATIONS

Bygdeman, M. , et al., "Replens Versus Dienoestrol Cream in the Symptomatic Treatment of Vaginal Atrophy in Postmenopausal Women", *Maturitas, Journal of the Climacteric & Postmenopause*, vol. 23 (3), (1996),259-263.

Milsom, I. , "Symptoms, Diagnosis and Treatment of Vaginal Atrophy", *Journal of the British Menopause Society*, vol. 08 (3), (2002),115-116.

Pandit, L. , et al., "Postmenopausal Vaginal Atrophy and Atrophic Vaginitis", *American Journal of the Medical Sciences*, vol. 314 (4), (Oct. 1997),228-231.

Van Der Laak, J. A. W., et al., "The Effect of Replens® on Vaginal Cytology in the Treatment of Postmenopausal Atrophy: Cytomorphology Versus Computerised Cytometry", *Journal of Clinical Pathology*, 55(6), (2002),446-4511.

* cited by examiner

*Primary Examiner*—Leigh C. Maier
(74) *Attorney, Agent, or Firm*—Schwegman, Lundberg & Woessner, P.A.

(57) ABSTRACT

The invention provides mannose phosphate and salts thereof for increasing vaginal cell growth, vaginal cell maturation and vaginal moisture, as well as compositions, articles and methods for treating and preventing vaginal conditions characterized by poor vaginal cell growth, low vaginal cell differentiation and low vaginal moisture.

11 Claims, 2 Drawing Sheets

COMPOSITIONS FOR VAGINAL TREATMENT

FIELD OF THE INVENTION

The invention relates to the use of compositions containing mannose phosphate to promote vaginal cell proliferation and maturation.

BACKGROUND OF THE INVENTION

Vaginal atrophy is a common and well-recognized problem in menopausal women. It is found in up to 50% post-menopausal women as well as in 10-20% pre-menopausal women with low estrogen levels. Vaginal atrophy is believed to be caused by low estrogen levels that result in a decrease in vaginal cell proliferation and differentiation. The decrease in cell proliferation leads to thinning of vaginal epithelium and to a lack of glycogen production by intermediate cells. Glycogen plays an important role in maintaining vaginal ecosystem by serving as food for *Lactobacilli acidophilus*, the normal flora in the vagina, and by serving as a substrate for acid production to maintain low vaginal pH. The thinning of vaginal epithelium and lack of glycogen in vaginal atrophy patients frequently results in vaginal dryness, discomfort and vaginitis.

While hormone replacement therapy has been used with some success to treat vaginal atrophy, new findings of the Women's Health Initiative Study indicate that such hormone replacement therapy increases the risk of heart attacks, stroke, blood clots, and breast cancer.

Therefore, a need exists for non-toxic compositions and methods to treat vaginal atrophy without the need for hormonal replacement therapies that can have negative side effects.

SUMMARY OF THE INVENTION

The present invention is directed to compositions and methods for treating and preventing vaginal conditions characterized by low vaginal cell proliferation, low vaginal cell differentiation, low vaginal moisture or vaginal atrophy. The compositions and methods of the invention employ mannose phosphate, which can promote vaginal cell proliferation and maturation.

Therefore, in some embodiments, the invention is directed to a composition comprising an effective amount of mannose phosphate and a pharmaceutically acceptable carrier. The compositions of the invention can promote vaginal cell growth, vaginal cell maturation and may be used to increase the thickness and restore the health of vaginal epithelium.

The invention is also directed to a method for treating or preventing a vaginal condition in a mammal. The method involves administering to a mammal an effective amount of a composition that includes a mannose phosphate or a salt thereof. As illustrated herein, the mannose phosphate or salt thereof can increase growth of mammalian epithelial cells and promote vaginal cell maturation. The compositions of the invention can therefore be used to treat conditions such as low vaginal cell proliferation, low vaginal cell differentiation or low vaginal moisture. In one embodiment, the condition is vaginal atrophy.

In one embodiment, the mannose phosphate employed is mannose-6-phosphate. As is known to one of skill in the art, mannose-6-phosphate can assume a number of conformations, all of which are contemplated by the invention. Some of the conformations that mannose-6-phosphate can assume are depicted below:

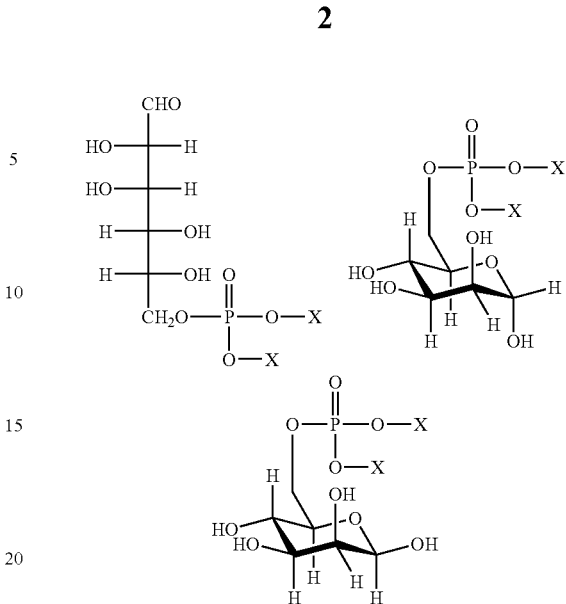

wherein X is a double bond, hydrogen or a cation. The cation can be a monovalent or divalent cation, for example, sodium, potassium, calcium, magnesium, manganese, zinc and the like.

Moreover, in some compositions of the invention some of the mannose phosphate molecules can have a variety of substituents in place of the hydroxy (—OH), aldehyde (—CHO), and hydrogen substituents that are generally found in mannose phosphate preparations. In general, the exact type of substituents on the mannose phosphate compound(s) of the invention can be varied to stimulate optimal levels of vaginal cell growth and/or maturation. Polymers of mannose-6-phosphate that can breakdown into monomers of mannose phosphate are also contemplated. Such polymers can include other saccharides or non-saccharides that breakdown to permit release of mannose phosphate.

The compositions of the invention are generally administered intravaginally. However, other routes are also contemplated. For example, the compositions can also be administered topically. The compositions can be incorporated into feminine products such as douches, tampons, foams, creams, sustained release implants and the like for easy use and administration. The invention further provides syringe-like applicators for administration of the compositions of the invention. Such applicators can contain a mannose phosphate composition of the invention. Douches, tampons, foams, creams, sustained release implants and applicators can be prepared in a sterile manner to optimize the shelf life of the composition and to permit the composition to be dispensed in a sterile manner.

An effective amount of the compounds of the invention can vary, but in some embodiments the effective amount of mannose phosphate can range from about 0.01 micrograms to about 500 milligrams.

DETAILED DESCRIPTION OF THE INVENTION

Figure 1:
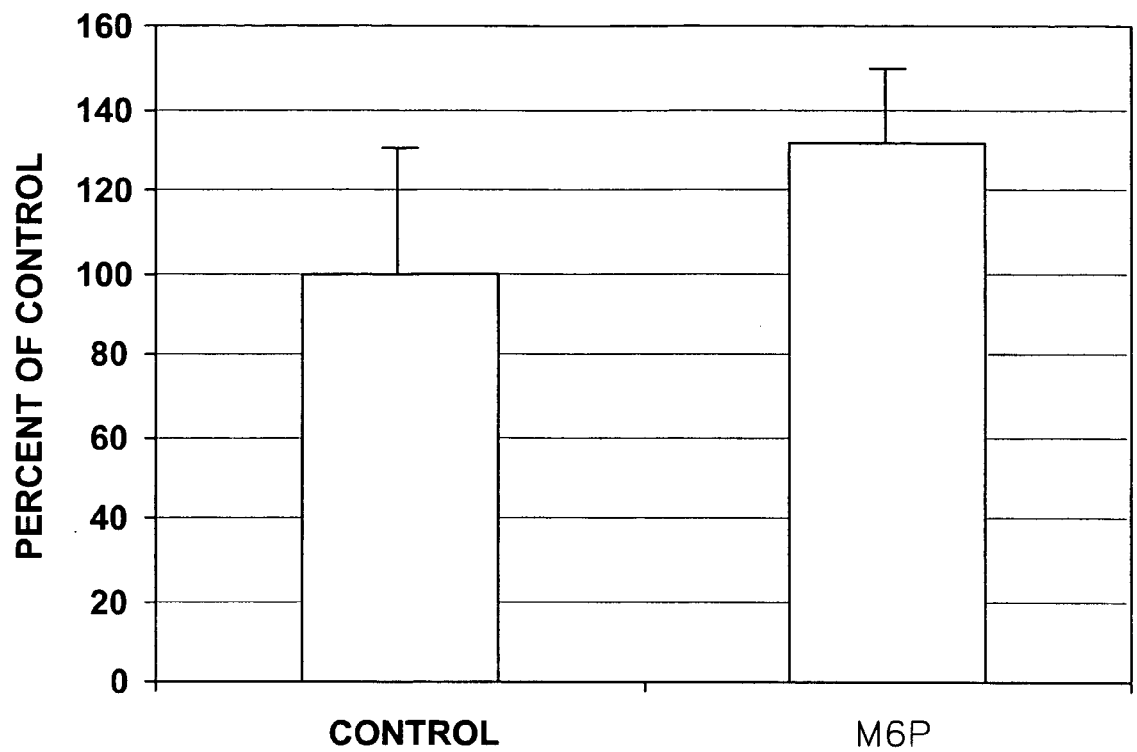
FIG. 1 illustrates the effect of mannos-6-phosphate (M6P) on cell proliferation in normal human vaginal epithelial cells in culture medium. Six samples were tested in each group; the error bar represents the standard deviation.

The invention provides compositions and methods to increase vaginal cell proliferation and vaginal cell differentiation or maturation. Such compositions can promote vaginal cell growth, the development of differentiated vaginal cells and may be used to increase the thickness and restore the health of vaginal epithelium. The compositions employed by the invention are inexpensive, non-toxic and readily available. The efficacy of these compositions and methods does not rely upon hormonal replacement or substances that are not naturally found in the body. Hence, the compositions avoid the negative side effects associated with commonly used hormone replacement therapies.

Mannose-Phosphate Compositions

Compositions employed by the invention for increasing vaginal cell proliferation and maturation contain a mannose phosphate, preferably mannose-6-phosphate (M6P).

In some embodiments, other saccharides can also be included in the compositions of the invention. For example, the mannose-phosphate compositions can include glucose-1-phosphate, glucose-6-phosphate, mannose-1-phosphate, galactose-6-phosphate, fructose-6-phosphate, glucose-1,6-diphosphate, or fructose-1,6-diphosphate. The percentage of alternate saccharides in the compositions of the invention can vary. For example, the compositions of the invention can include 0% to about 50% alternate saccharides. In other embodiments, the compositions of the invention can include about 0% to about 40%, or 0% to about 30%, or 0% to about 20% or 0% to about 10% alternate saccharides.

Moreover, the mannose phosphate for use in the present invention can be formulated as pharmaceutically or cosmetically acceptable salts thereof, e.g., mono- or disodium salts, as well as any precursor forms that when applied to the epithelium or skin release the mannose phosphate.

In some embodiments some of the mannose phosphate sugar units can have a variety of substituents in place of the hydroxy (—OH), aldehyde (—CHO), and hydrogen substituents that are typically found on mannose phosphate. For example, lower alkyl moieties can replace any of the hydrogen atoms from the hydroxy (—OH) or hydrogen substituents of the mannose phosphate compounds employed in the invention. Amino or lower alkyl amino groups can replace any of the OH or hydrogen groups of the mannose phosphate compounds employed in the invention. Sulfate ($SO_4^-$) may replace the phosphate groups of the mannose phosphate compounds employed in the invention. Hence, substituents that can be present instead of, or in addition to, the substituents typically present on mannose phosphate compounds include sulfate ($SO_4^-$), lower alkoxy, lower alkanoyloxy, and/or lower alkanoylaminoalkyl.

As used herein, lower alkyl means ($C_1$-$C_6$) alkyl. Such ($C_1$-$C_6$) alkyl can be methyl, ethyl, propyl, isopropyl, butyl, iso-butyl, sec-butyl, pentyl, 3-pentyl, or hexyl. Preferred lower alkyl groups are ($C_1$-$C_3$) alkyl including methyl ethyl, propyl, isopropyl and the like. Lower alkoxy generally means ($C_1$-$C_6$) alkoxy; such ($C_1$-$C_6$) alkoxy can, for example, be methoxy, ethoxy, propoxy, isopropoxy, butoxy, iso-butoxy, sec-butoxy, pentoxy, 3-pentoxy, or hexyloxy. Lower hydroxy alkyl refers to a hydroxy group attached to a lower alkyl or lower alkylene group (e.g. —$CH_2$—$CH_2$—OH). Lower alkanoyloxy refers to ($C_2$-$C_6$) alkanoyloxy, for example, acetoxy, propanoyloxy, butanoyloxy, isobutanoyloxy, pentanoyloxy, or hexanoyloxy. Lower ($C_1$-$C_6$) alkanoylamino can, for example, be acetamino, propanoylamino, butanoylamino, isobutanoylamino, pentanoylamino, or hexanoylamino.

Therefore, while the active ingredients in the compositions of the invention typically include a high percentage of mannose phosphate, some variability in the types of substituents and sugar units present in the mannose phosphate preparation employed is acceptable so long as the preparation can increase vaginal cell proliferation or maturation.

In other embodiments, polymers and mixtures of mannose phosphate with other polymers can be employed in the compositions and methods of the invention. Polymers of mannose phosphate that can breakdown to release mannose phosphate monomers are particularly desirable. In some embodiments, non-saccharide polymers can be used in the mannose phosphate formulations. Examples of polymers that can be used with mannose phosphate include proteoglycans, poly(ethylene glycol)/poly(ethylene oxide), poly(vinyl alcohol), poly(vinylpyrrolidone), and poly(2-hydroxyethyl methacrylate). Such polymers can be covalently bonded to mannose phosphate or simply combined with mannose phosphate to form a mixed composition.

Methods of Use

The present invention is directed to methods of treating or preventing or otherwise ameliorating vaginal conditions characterized by poor vaginal cell growth, low vaginal moisture and poor vaginal cell differentiation. The compositions of the invention can also be used in vaginal moisturizers and in methods for moisturizing the vagina to relieve vaginal dryness and restore health to the vaginal epithelium.

In some embodiments, the compositions and methods of the invention are used in subjects with an abnormally thin vaginal lining or subjects with an abnormally thin vaginal mucosa. Symptoms resulting from the abnormally thin vaginal lining or mucosa include vaginal dryness, discomfort, itching, dyspareunia, infection, inflammation, ulcers, discharge, and bleeding. In some instances, the compositions and methods of the invention are used to treat vaginal atrophy.

Vaginal atrophy is a condition occurring in some women, typically postmenopausal women, in which there is significant thinning of the mucosa of the vagina. The thin vaginal mucosa lacks maturation, meaning that it consists of numerous parabasal cells and little or no superficial and intermediate cells, which results in decreased glycogen deposits and a higher pH. Vaginal atrophy is caused chiefly by an estrogen deficiency because the mucosa of the vagina is an estrogen sensitive tissue and a well-known target organ for estrogen. As provided herein, vaginal atrophy and the effects of low estrogen on the vagina can be reversed by treatment with the compositions and methods of the invention.

These methods include administering to the animal an effective amount of mannose phosphate, for example, a therapeutically effective amount of mannose phosphate. According to the invention, a therapeutically effective amount of mannose phosphate can increase vaginal epithelial cell growth, increase the percentage of differentiated or mature vaginal epithelial cells and increase vaginal moisture.

Treatment of, or treating, a vaginal condition is intended to include the alleviation of or diminishment of at least one symptom typically associated with the vaginal condition, for example, at least one symptom typically associated with vaginal atrophy. The treatment also includes alleviation or diminishment of more than one symptom. Ideally, the treatment cures, e.g., substantially eliminates one or more symptoms associated with the vaginal condition.

Administration

According to the invention, mannose phosphate compounds, polymers, co-polymers, polymer mixtures and their salts, can promote vaginal cell proliferation and/or vaginal cell maturation in animals. The term "animal," as used herein, refers generally to a warm-blooded animal. Mammals include cattle, buffalo, sheep, goats, pigs, horses, dogs, cats, rats, mice, rabbits, chickens, turkeys, and humans. Also included are other livestock, domesticated animals and captive animals.

An effective amount of a mannose phosphate compound, polymer, co-polymer, polymer mixture or salts thereof, for promoting vaginal cell growth and/or maturation is an amount that increases the growth of a population of vaginal cells, for example, epithelial cells, relative to a population of the same type of vaginal cells that received no mannose phosphate. To achieve the desired inhibition, the composition may be administered as single or divided dosages, for example, of at least about 0.001 µg to about 100 to 200 mg, of about 0.01 µg to about 75 to 100 mg, of about 0.1 µg to about 50 to 75 mg or about 1.0 µg to about 30 to about 50 mg of one or more mannose-6-phosphate compound, although other dosages may provide beneficial results. In some embodiments, the dosage can vary from about 0.01 mg to about 50 mg.

Daily doses of the compositions of the invention can vary as well. Such daily doses can range, for example, from about 0.001 mg/day to about 500 mg/day, from about 0.01 mg/day to about 250 mg/day, from about 0.01 mg/day to about 120 mg/day, from about 0.1 mg/day to about 100 mg/day, from about 0.1 mg/day to about 75 mg/day, and from about 0.1 mg/day to about 50 mg/day of one or more of the mannose phosphate compounds.

The amount administered will vary depending on various factors including, but not limited to, the disease, the weight, the physical condition, the health, the age of the animal, and whether prevention or treatment of vaginal atrophy is to be achieved. Such factors can be readily determined by the clinician employing animal models or other test systems that are available in the art.

The compositions of the invention can be administered for prophylactic, therapeutic, and/or hygienic use. Such administration can be topical, vaginal, rectal, and other convenient routes. Administration can be directly to epithelial cell surfaces. For example, the compositions of the invention can be administered directly to mucosal surfaces. Mucosal surfaces include vaginal, urogenital, rectal and the like. Surfaces of the urogenital tract that can be treated with the compositions and methods of the invention include rectal, urethral, ureteral, vaginal, cervical, uterine, etc. In many embodiments, the epithelial cell surface is vaginal.

Administration of the therapeutic agents in accordance with the present invention may be in a single dose, in multiple doses, in a continuous or intermittent manner, depending, for example, upon the recipient's physiological condition, whether the purpose of the administration is therapeutic or prophylactic, and other factors known to skilled practitioners. For prevention of certain conditions or diseases (e.g. vaginal atrophy), administration of the compositions of the invention may be essentially continuous over an indeterminate period of time, for example, at regular intervals for life. Alternatively, the compositions of the invention can be administered continuously for a pre-selected period of time or in a series of spaced doses. Local administration is generally contemplated.

The compositions are prepared by combining the active ingredients in the appropriate concentrations. Other active or inactive agents selected by one of skill in the art can optionally be added. The absolute weight of a given active agent included in a unit dose can vary widely.

The compositions of the invention can be administered in the form of an article or carrier such as a vaginal insert, or by way of a syringe-like applicator, tablet, suppository, pessary, powder/talc or other solid, solution, liquid, spray, aerosol, douche, ointment, tampon, foam, cream, gel, paste, microcapsule(s), vaginal sponge, vaginal ring, controlled release formulation, sustained release formulation or bioadhesive gel (e.g., a mucoadhesive thermogelling composition (see, for example, U.S. application Ser. No. 10/135805, filed on Apr. 30, 2002, which is incorporated herein by reference)).

For intravaginal administration, the therapeutic agents may be formulated as is known in the art for direct application to the vaginal area. Forms chiefly conditioned for vaginal application take the form, for example, of creams, milks, gels, dispersions, micro-emulsions, lotions thickened to a greater or lesser extent, impregnated pads, ointments, aerosol formulations (e.g., sprays or foams), creams, lotions, pastes, jellies, sprays, and aerosols. Alternatively, the composition can be formulated to be part of an adhesive polymer, such as polyacrylate or acrylate/vinyl acetate copolymer.

Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents. Liquid sprays are conveniently delivered from pressurized packs, for example, via a specially shaped closure. The active compositions can also be delivered via iontophoresis, e.g., as disclosed in U.S. Pat. Nos. 4,140,122; 4,383,529; or 4,051,842. The percent by weight of a prophylactic agent of the invention present in a formulation will depend on various factors, but generally will be from about 0.01% to about 98% of the total weight of the formulation, and typically about 0.1 to about 90% by weight.

The pharmaceutical formulations of the present invention may include, as optional ingredients, pharmaceutically acceptable carriers, diluents, solubilizing or emulsifying agents, and salts of the type that are available in the art. Examples of such substances include normal saline solutions such as physiologically buffered saline solutions and water. Specific non-limiting examples of the carriers and/or diluents that are useful in the pharmaceutical formulations of the present invention include water and physiologically acceptable buffered saline solutions such as phosphate buffered saline solutions with a pH of about 4.5 to about 5.5.

Furthermore, the active ingredients may also be used in combination with other therapeutic agents, for example, anti-microbial agents, pain relievers, anti-inflammatory agents, vitamins (e.g., vitamin B, C or E), aloe vera and the like, whether for conditions described herein or some other condition. Previous work by the inventors has shown that hyaluronic acid compositions can inhibit pathogen attachment to a variety of cell types, including vaginal epithelial cells. See U.S. Ser. No. 10/401,522 and U.S. Ser. No. 10/608,848, which are incorporated herein by reference. Moreover, the inventors have shown that hyaluronic acid can promote vaginal cell growth and maturation. See U.S. Ser. No. 10/696,547, which is incorporated herein by reference. Hence, according to the invention, compositions containing mannose phosphate can also contain hyaluronic acid.

The present invention further pertains to a packaged pharmaceutical composition for controlling or preventing a vaginal condition (e.g. vaginal atrophy) such as a kit or other container. The kit or container holds a therapeutically effective amount of a pharmaceutical composition for preventing, controlling or inhibiting the vaginal condition and instructions for using the pharmaceutical composition for prevention, control or inhibition of the vaginal condition. The pharmaceutical composition includes mannose phosphate, in a therapeutically effective amount such that the vaginal condition is prevented, controlled or inhibited.

In addition, the invention provides a vaginal insert that can release the mannose phosphate in a controlled fashion. Such a vaginal insert can be biodegradable or non-biodegradable. The vaginal insert provides sustained release of the active ingredients at an appropriate rate for achieving the desired degree of vaginal cell growth or vaginal cell maturation, or of the desired degree of vaginal atrophy prevention or treatment.

In some embodiments, the active ingredients can be formulated with oleaginous bases or ointments to form a semisolid composition with a desired shape. For example, the composition can be shaped for easy insertion into an orifice such as the vagina. This class of formulations comprises the active ingredients and hydrocarbon-based semisolids containing dissolved and/or suspended bacteriostats/preservatives and a buffer system. The petrolatum component in these bases can be any paraffin ranging in viscosity from mineral oil employing incorporated isobutylene, colloidal silica, or stearate salts to paraffin waxes. White and yellow petrolatums are examples of such petrolatum components. Bases of this class can be made by incorporating high-melting waxes into a fluid mineral oil via fusion or by incorporation of polyethylene into mineral oil at elevated temperature. Polysiloxanes (also known as silicones) are suitable for use in these bases and typically have a viscosity in the range of about 0.5 to $10^6$ centistokes. The organic entities attached to the polysiloxane are preferably lower molecular weight hydrocarbon moieties having from 1 to 8 carbons each, such as lower alkyl, lower alkenyl, phenyl and alkyl substituted phenyl, and phenyl(lower) alkyl, such as benzyl. In such a moiety, each lower alkyl or alkenyl group preferably has 1 to 3 carbons inclusive, such as in a dimethylsiloxane polymer.

Absorption bases can be used with such an oleaginous system. In addition to the active ingredients, additional ingredients with the capacity to emulsify a significant quantity of water are employed. Water-in-oil (w/o) emulsions can be formed wherein the external phase is oleaginous in character. Preservatives/bacteriostats, such as the parabens, buffer systems, etc. can be incorporated into these bases as emulsified aqueous solutions together with the active ingredient. Diverse additives are conveniently used as the emulsifier, and these include, but are not limited to, cholesterol, lanolin (which contains cholesterol and cholesterol esters and other emulsifiers), lanolin derivatives, beeswax, fatty alcohols, wool wax alcohols, low HLB (hydrophobe/lipophobe balance) emulsifiers, and assorted ionic and nonionic surfactants, singularly or in combination.

Water-In-Oil emulsion bases can be employed in the compositions, inserts and articles of the invention. These formulations can be an expansion of the general class of absorption bases that includes liquids or creams. They can be prepared by taking a mixture of the active ingredients with oil phase ingredients, bacteriostats/preservatives and buffer salts that are dissolved or suspended therein and to which water has been added to form a water-in-oil emulsion.

Oil-In-Water emulsion bases can also be utilized in the compositions, inserts and articles of the invention. These systems are semisolid emulsions, micro-emulsions, or foam emulsion systems. Usually such a system has a "creamy white" appearance. Typically, the internal oil phase is in the range in percentage composition of about 10% to about 40% oil by weight and the external phase may contain 80% or more water. The oleaginous phase may contain, but is not limited to, long-chain alcohols (cetyl, stearyl), long-chain esters (myristates, palmitates, stearates), long-chain acids (palmitic, stearic), vegetable and animal oils and assorted waxes. These can be made with anionic, cationic, nonionic or amphoteric surfactants, or with combinations especially of the nonionic surfactants.

Inserts and suppositories containing the active ingredients can be, for example, oleaginous in nature that melt at body temperature, or polyethylene glycol-based compositions that dissolve in mucosal (e.g. vaginal) fluids. Additional bases for suppositories are glycerin and glycerinated gelatin.

The active ingredients can be formulated into inserts, articles, tampons, transdermal patches, bandages, and dressings using buffered gels made with gelling agents. Some examples of these gelling agents are: cellulosics, cationic polymers, polyoxyalkylenes, and carboxyvinyl polymers. Cellulosics useful in the formulations of the invention include, for example, methyl cellulose, carboxymethyl cellulose, hydroxyethyl cellulose, and hydroxypropyl cellulose. Cationic Polymers useful in the formulations of the invention include "Polyquaternium-10", a polymeric quaternary ammonium salt of hydroxyethyl cellulose reacted with a trimethyl ammonium-substituted epoxide, and the like. Polyoxyalkylenes useful in the invention include polyoxyethylene-polyoxypropylene esters of lanolin and derivatives thereof. Carboxyvinyl polymers useful for the formulations of the invention include cross-linked acrylic acid polymers, e.g., those commercially available from B. F. Goodrich Co., Akron, Ohio, under the designation CARBOPOL™.

Controlled or sustained release can be achieved by the addition of time-release additives, such as polymeric structures, matrices, that are available in the art. For example, the compositions of the invention may also be administered through the use of hot-melt extrusion articles, such as bioadhesive hot-melt extruded film (see, for example, U.S. Pat. No. 6,375,963, which is incorporated herein by reference). The formulation can comprise a cross-linked polycarboxylic acid polymer formulation, generally described in U.S. Pat. No. 4,615,697 to Robinson (hereinafter "the '697 patent"), which is incorporated herein by reference. In general, about eighty percent of the monomers of the polymer in such a formulation contain at least one carboxyl functionality. The cross-linking agent should be present at such an amount as to provide enough adhesion to allow the system to remain attached to the target epithelial or endothelial cell surfaces for a sufficient time to allow the desired release of mannose phosphate to take place.

An insert or article can comprise a mixture or coating of polymers that provide release of the active agents at a constant rate over a prolonged period of time. In some embodiments, the article or insert comprises water-soluble pore forming agents, such as polyethylene glycol (PEG) that can be mixed with water insoluble polymers to increase the durability of the insert and to prolong the release of the active ingredients. Such a water-soluble pore-forming agent can be polyethylene glycol, polypropylene glycol, a mixture or polymer of sugars (lactose, sucrose, dextrose, etc.), salts, poloxamers, hydroxypropylcellulose, polyvinyl alcohol and other water-soluble food grade and other excipients.

When PEG is used as a pore forming agent, the molecular weight of PEG is in the range from about 200 to about 20,000, alternatively, from about 400 to about 8,000. For example, PEG having a molecular weight of about 540 to about 8,000 is used. In another embodiment, the PEG has a molecular weight of about or above 1,000 to about 8,000. The molecular weight of PEG used for the coating with the formulation of the invention will depend on the ability of PEG to form a coating film that is non-sticky, having enough strength and creating adequate pore size for controlling the release of active ingredients over the desired time period both in vitro and in vivo.

The pore-forming agent is used in the formulation of the invention in the amount effective to regulate the release of a mannose phosphate compound at a desired rate. Preferably, the effective amount of the pore-forming agent provides long term delivery of the active agent thus increasing the useful life of a sustained-release insert, article or implant. The effective amount of the pore forming agent will depend on the desired rate and duration of the release and the ability to form a continuous microporous film during the coating process. To enable release duration over longer periods of time PEG with higher molecular weights is used. For example, PEG 8000 can provide release over a period of time that is longer than 100 days, when used in a concentration from 10 to 50%, preferably from 20 to 45% and most preferably from 30 to 45%. The concentration of PEG is expressed herein in % weight per dry basis and represents the concentration of PEG in the coating film after drying.

Similarly, the thickness of the coating film is from 5 to 50 µm, preferably 30 from 10 to 30 µm and most preferably from 15 to 25 µm.

A good correlation exists between the dissolution rate of active agents and the amount of pore forming agent incorporated in the coating film based on in vitro and in vivo studies. Depending on the desired length of release, the PEG concentration ranges can be adjusted as needed. For example, in vivo duration of a coated insert may be predicted simply from the in vitro dissolution rate of the active agent at the 120-hour time point.

The inserts and articles of the invention may also comprise a water insoluble polymer. Examples of such polymers are ethylcellulose, acrylic resins, co-polymer of methacrylic acid and acrylic acid ethyl ester, polylactic acid, PLGA, polyurethane, polyethylene vinyl acetate copolymer, polystyrene-butadiene copolymer and silicone rubber, or mixtures thereof. For example, polymers sold under trade names Aquacoat ECD 30 and Eudragit RS 30 and NE 30D (registered trademarks of Rhom Tech, Inc.) can be used.

A polymer suitable for use in this invention is a polymer that can release the active agents of the invention at a rate that is sufficient for treatment of a vaginal condition described herein. The rate controlling formulation prepared with such a polymer is stable during implantation. The formulation should have enough strength to withstand routine handling, and have the stability to release the active ingredients at an acceptable rate.

In one embodiment, the coating formulation of the invention is used to coat pellets comprising the active ingredients that are compressed to form a solid, biodegradable insert and then administered for promoting vaginal cell proliferation or maturation.

A polymer formulation can be utilized to provide controlled or sustained release. Such a polymer formulation can be adjusted to control the release rate of the mannose phosphate by varying the amount of cross-linking agent in the polymer. Suitable cross-linking agents include divinyl glycol, divinylbenzene, N,N-diallylacrylamide, 3,4-dihydroxy-1,5-hexadiene, 2,5-dimethyl-1,5-hexadiene and similar agents.

One example of a polymer for use in such a formulation is Polycarbophil, U.S.P., which is commercially available from B. F. Goodrich Specialty Polymers of Cleveland, Ohio under the trade name NOVEON™-AA1. The United States Pharmacopeia, 1995 edition, United States Pharmacopeial Convention, Inc., Rockville, Md., at pages 1240-41, indicates that polycarbophil is a polyacrylic acid, cross-linked with divinyl glycol.

Other useful bioadhesive polymers that may be used in such a drug delivery system formulation are mentioned in U.S. Pat. No. 4,615,697. For example, these include polyacrylic acid polymers cross-linked with, for example, 3,4-dihydroxy-1,5-hexadiene, and polymethacrylic acid polymers cross-linked with, for example, divinyl benzene. Typically, these polymers would not be used in their salt form, because this would decrease their bioadhesive capability. Such bioadhesive polymers may be prepared by conventional free radical polymerization techniques utilizing initiators such as benzoyl peroxide, azobisisobutyronitrile, and the like. Exemplary preparations of useful bioadhesives are provided in the '697 patent.

For vaginal administration, the formulation preferably degrades slowly or remains attached to the epithelial or endothelial cell surfaces for a period of at least about one to about forty-eight hours. Such results may be measured clinically over various periods of time, by testing samples from the vagina for mannose phosphate. Bioadhesion of a formulation of the invention can be attained with bioadhesive polymers using a cross-linking agent that is present at about 0.1 to 6.0 weight percent of the polymer, with about 1.0 to 2.0 weight percent in some embodiments, to achieve an appropriate level of bioadhesion. Bioadhesion can also be measured by commercially available surface tensiometers utilized to measure adhesive strength.

The formulation may be in the form of a gel, cream, tablet, capsule, suppository, film, or any other pharmaceutically acceptable form that is tolerated by epithelial cells (e.g. the mucosa) and does not wash away easily. Different formulations are further described in U.S. Pat. No. 4,615,697, which is incorporated herein by reference.

As will be apparent to those skilled in the art, the composition of the formulation can be varied to affect certain properties of the formulation. For example, the viscosity can be varied by adding a polymer or gel former. In some embodiments, a bioadhesive polymer can be included at various concentrations to provide greater or lesser bioadhesion. A pH sensitive bioadhesive can be utilized to effect greater release at certain pH values. The particular bioadhesive qualities should prevent the composition from being diluted or washed away, thereby increasing the utility of the present formulation.

Liquid compositions of the invention can be administered from absorbent materials, such as a bandage, tampon or sponge, or as a spray/aerosol (applied to the affected area using a pump-type or aerosol sprayer). The use of a tampon, in which the composition of the invention has been incorporated, is advantageous in that it the composition will be slowly and continuously released even though it may be continuously carried away by menstrual blood or other vaginal discharge. Providing the composition in the form of a solution, which may initially be provided in a concentrated liquid form, or as a dissolvable powder, tablet or the like requiring the addition of water, saline or other suitable diluents prior to use, enables the composition to be administered as a vaginal douche.

Solid compositions of the invention can be applied by any number of means, including the use of applicators or by patient self-insertion. For example, creams, lotions, suppositories, foams, pastes, ointments, gels, tablets, or tampons may be administered using an applicator, such as a squeeze-type or plunger-type applicator. Administering the composition as a vaginal suppository is advantageous as it provides convenience, ease of application, increased safety and/or neatness. Administering the composition as a cream having low surface tension is advantageous as it provides a uniform wetting action that assists in composition penetration into crypts and crevices of the orifice. Such a creamy composition can also act as a moisturizer.

Additionally, additives may be mixed in with the formulation for maximum or desired efficacy of the delivery system or for the comfort of the patient. Such additives include, for example, lubricants, plasticizing agents, preservatives, gel formers, tablet formers, pill formers, suppository formers, film formers, cream formers, disintegrating agents, coatings, binders, vehicles, coloring agents, taste and/or odor controlling agents, humectants, viscosity controlling agents, pH-adjusting agents, and similar agents.

Figure 3:
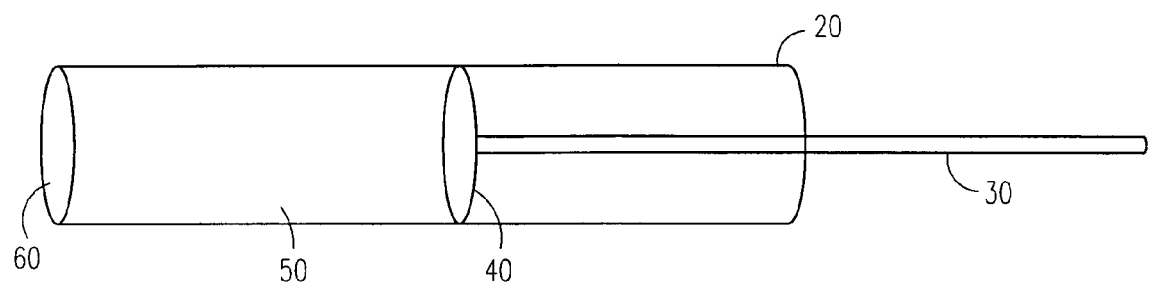
FIG. 3 is a schematic diagram of one type of syringe-like applicator that can be used to deliver a mannose phosphate composition to a vagina of a mammal. The syringe-like applicator consists of a barrel 20 and a plunger 30 with a plunger head 40. The syringe-like applicator can also have a barrier seal 60 distal to the plunger head 40. The syringe-like applicator can also have a chamber 50 within the barrel that lies between the plunger 30 and the barrier seal 60. The chamber 50 comprises an effective amount of a mannose phosphate compound or a salt thereof. The presence of the barrier seal 60 seals the applicator and keeps the composition contained with the applicator during shipping and handling. The barrier seal 60 can be removed by the user, or it can rupture when the user depresses the plunger. At the time of use, the applicator is inserted into the vagina and the plunger 30 is depressed. This force will push the composition out of the applicator and into the vagina.
Figure 4:
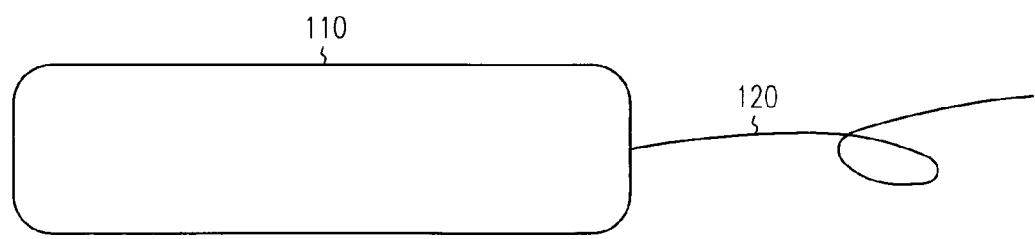
FIG. 4 is a schematic diagram of a vaginal insert that can be used to deliver a mannose phosphate composition to the vagina of a mammal. The vaginal consists of a tubular shaped material 110 comprising a mannose phosphate compound and a string 120 or other attachment for retrieval or positioning of the vaginal insert within the vagina. In some embodiments, the string 120 is optional, for example, because the vaginal insert slowly dissolves, breaks down or erodes to provide sustained release of mannose phosphate. Hence, retrieval may not be needed. The syringe-like applicator illustrated in FIG. 3 may be used for delivery of the vaginal insert.

One desirable embodiment provides for compositions of the invention in a syringe-like applicator (also known as a plunger-type or syringe-like applicator (see FIG. 3)). For example, a composition including mannose phosphate may be placed into a chamber 50 within the barrel 20 of a syringe-like applicator. The chamber is sealed at the distal end with a barrier seal 60 and at the proximal end by the plunger head 40. The presence of the barrier seal 60 seals the applicator and keeps the composition contained with the applicator during shipping and handling. However, the barrier seal 60 can be removed by the user or it can rupture when the user depresses the plunger 30. At the time of use, the applicator is inserted into the vagina and the plunger 30 is depressed. This force will push the composition out of the applicator and into the vagina. As an alternative, a tapered tip can be used in place of the barrier seal 60.

One embodiment of the invention provides an aqueous gel containing a mucoadhesive material, such as carboxymethylcellulose (optionally mixed with a thermogelling mucoadhesive agent), to be mixed with mannose phosphate to thereby form a composition of the invention. An additional embodiment provides for the encapsulation of mannose phosphate in polymeric microparticles. Once in situ, the polymer dissolves and the mannose phosphate is released. In this case, release of mannose phosphate can be controlled by the microparticles to provide extended production of the desired product (e.g., sustained release). The delivery vehicle is not limited to use in the vagina, but could also be applied to a wide variety of biomedical applications where delivery of mannose phosphate is desired. Appropriate modification of the delivery vehicles described herein is within the skill of those in the art.

Additionally, the composition and/or delivery materials may contain additional beneficial agents that can improve the health of the vagina. For example, polymers used as carrier or for encapsulation or for sustained release may be hydrolytically degraded into an acid or acid producing species. One such polymer is a poly (vinyl alcohol) backbone with pendant polycaprolactone chains that, upon disintegration, yields poly [vinyl (polycaprolactate)]. The polycaprolactone is hydrolytically degraded into caproic acid. This acid aids in lowering pH and controlling harmful bacterial growth, thus helping to restore balance to the epithelium. In addition, this material is melt processable and can be formed into a system for controlled delivery of the mannose phosphate. Additionally, a peroxide of Laureth-4 (e.g., a Laureth-4 terminal peroxide) would release laureth-4 and peroxide (e.g., hydrogen peroxide). Laureth-4 decreases TSS-1 production by *S. aureus* and the peroxide is available to suppress undesirable anaerobes and *Gardnerella vaginalis*, thus reducing toxin production while reestablishing the vaginal flora.

The Examples further illustrate certain aspects of the invention and are not intended to limit the invention in any manner.

EXAMPLE

Mannose-6-Phosphate Promotes Vaginal Cell Proliferation and Maturation

This Example describes experiments showing that mannose phosphates can promote vaginal cell proliferation and vaginal cell maturation.

Materials and Methods

Normal human vaginal epithelial cells from Clonetics (NHVE 5164) were subcultured in basal PrEBM (Clonetics CC 3165) within 96 well plates at 37° C., 5% $CO_2$. Cells were then exposed to medium containing mannose-6-phosphate (Sigma, M3655) at a concentration of $10^{-5}$ M. Control groups received culture medium without mannose-6-phosphate. Cell proliferation was examined three days later and glycogen positive cells were detected five days after mannose-6-phosphate treatment.

Cell proliferation was examined by using CellTiter 96 Aqueous One Solution from Promega (#TB245). Twenty μl of the reagent was added to each well. The plates were returned to cell culture incubator for 3 hours. The absorbance in each well was measured at 490 nm with a microtiter reader.

A periodic acid Schiff (PAS) assay was used to detect glycogen levels. Before the assay, cells were washed with PBS and fixed with a 10 vol % Formalin/ethanol solution for 1 hour at room temperature, followed by continuous rinsing with deionized (DI) water for 1 minute. A Harleco® PAS Assay Kit (from EM Science 64945/43) was used for glycogen detection. The basic principle is that the hydroxy groups on the glycogen units were first oxidized into aldehyde groups by periodic acid, and the aldehyde groups reacted with Schiff's agent to produce a red colorant. The specific assay operations were all done at room temperature as follows:

1. Periodic acid reagent was added to the well/chamber and allowed to stand for 10 minutes.
2. Samples were continuously rinsed in water for one minute.
3. Schiff's reagent was added and the samples were allowed to stand for 15 minutes.
4. Samples were continuously rinsed in deionized water for one minute.
5. Sodium carbonate reagent (diluted 2× with deionized water) was added and samples were allowed to stand for 5 minutes.
6. Samples were continuously rinsed in deionized water for 5 minutes.
7. Light Green SF Yellowish reagent was added and samples were allowed to stand for 30 seconds.
8. Samples were rinsed in deionized water briefly for 10 seconds.
9. Samples were dehydrated with a series of ethanol/water mixtures (75%, 90%, 95% to 100% ethanol) and xylene.
10. Samples were mounted with mounting medium.

The numbers of glycogen-stained positive cells were manually counted under microscope. The data was analyzed by student's t test, and p<0.05 was considered significant.

Results

Figure 2:
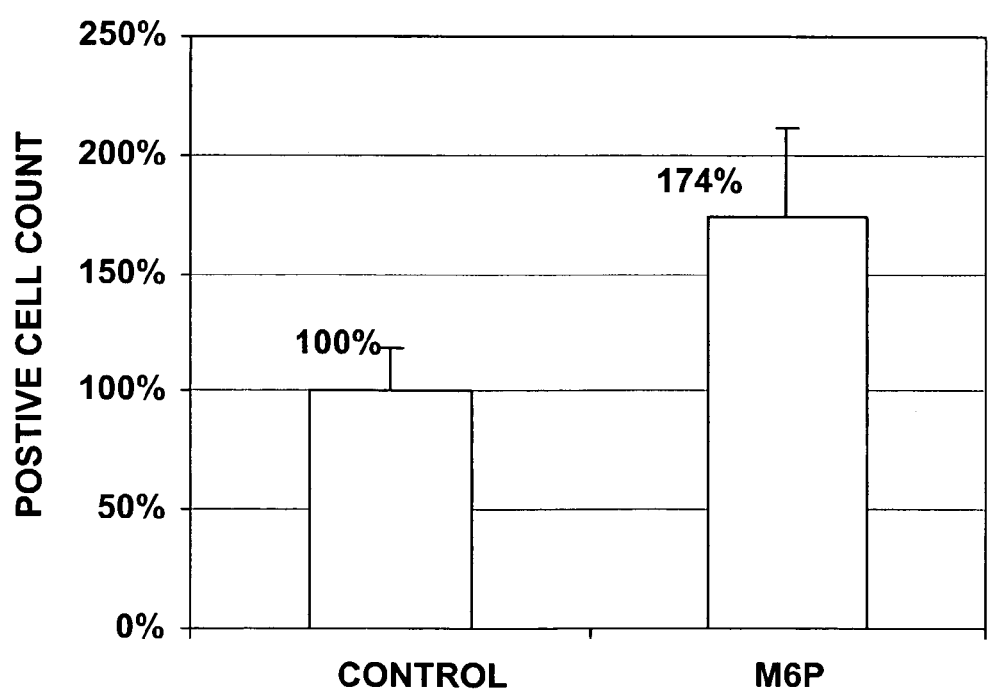
FIG. 2 illustrates that mannos-6-phosphate (M6P) treatment increases the observed numbers of mature vaginal epithelial cells as measured by glycogen production. Glycogen production in vaginal epithelial cell cytoplasm is a differentiation/maturation marker for vaginal epithelial cells. Each group had 5 samples and the error bar represents the standard deviation.

As shown in FIG. 1, mannose-6-phosphate treatment significantly (p<0.05) increased vaginal cell proliferation. Moreover, the number of glycogen-positive cells was significantly higher when vaginal cells were treated with mannose-6-phosphate (FIG. 2).

These results indicate that mannose-6-phosphate can stimulate cell proliferation and vaginal cell maturation. Vaginal atrophy is the thinning of the vaginal epithelium that may be caused by low estrogen levels resulting in a decrease in vaginal cell proliferation. Atrophic vaginitis, the overgrowth of pathogens due to the thinning of protective epithelium, can evolve in patients having vaginal atrophy. Hence, compositions containing mannose-6-phosphate that stimulate vaginal cell proliferation may be used to increase the thickness of vaginal epithelium, stimulate maturation of differentiated vaginal cells and restore healthy vaginal epithelium.

All patents and publications referenced or mentioned herein are indicative of the levels of skill of those skilled in the art to which the invention pertains, and each such referenced patent or publication is hereby incorporated by reference to the same extent as if it had been incorporated by reference in its entirety individually or set forth herein in its entirety. Applicants reserve the right to physically incorporate into this specification any and all materials and information from any such cited patents or publications.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. The methods and processes illustratively described herein suitably may be practiced in differing orders of steps, and that they are not necessarily restricted to the orders of steps indicated herein or in the claims. As used herein and in the appended claims, the singular forms "a," "an," and "the" include plural reference unless the context clearly dictates otherwise. Thus, for example, a reference to "an antibody" includes a plurality (for example, a solution of antibodies or a series of antibody preparations) of such antibodies, and so forth. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

What is claimed:

1. A method for treating vaginal atrophy, promoting vaginal epithelial cell proliferation and/or promoting vaginal epithelial cell differentiation in a patient in need thereof, comprising intravaginally administering to the patient an effective amount of a composition comprising mannose phosphate or a salt thereof, wherein the mannose phosphate or salt thereof can increase growth of mammalian epithelial cells.

2. The method of claim 1, wherein the vaginal atrophy comprises low vaginal moisture.

3. The method of claim 1, wherein the composition can increase production of glycogen by vaginal epithelial cells.

4. The method of claim 1, wherein the mannose phosphate is mannose-6-phosphate.

5. The method of claim 1, wherein the mannose phosphate is a compound of the formula:

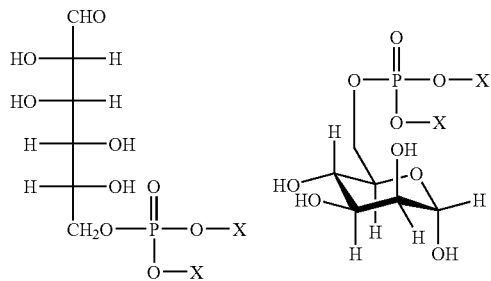

-continued

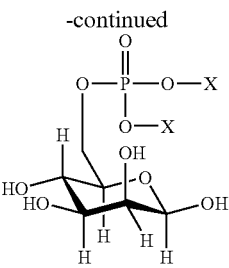

wherein X is a monovalent or divalent cation.

6. The method of claim 1, wherein the mannose phosphate is mixed with or covalently linked to a polymer.

7. The method of claim 6, wherein the polymer is poly (ethylene glycol), poly(vinyl alcohol), poly(vinylpyrrolidone), or poly(2-hydroxylethyl methacrylate).

8. The method of claim 1, wherein the effective amount comprises about 0.001 micrograms to about 500 milligrams of mannose phosphate or salt thereof.

9. The method of claim 1, wherein the composition further comprises an anti-bacterial, anti-fungal or anti-viral agent.

10. The method of claim 1, wherein the composition further comprises hyaluronic acid.

11. The method of claim 1, wherein the composition is a lotion, cream, gel or suspension.

* * * * *